United States Patent [19]

Bedingham et al.

[11] Patent Number: 5,333,609
[45] Date of Patent: Aug. 2, 1994

[54] CATHETER AND PROBE-CATHETER ASSEMBLY

[75] Inventors: William Bedingham, Maplewood; Joel R. Dufresne, St. Paul, both of Minn.; David F. Wirt, Prescott, Wis.

[73] Assignee: Minnesota Mining and Manufacturing Company, St. Paul, Minn.

[21] Appl. No.: 885,713

[22] Filed: May 19, 1992

[51] Int. Cl.⁵ .................................. A61B 5/00
[52] U.S. Cl. ......................... 128/632; 128/637
[58] Field of Search ...................... 128/633–635, 128/637, 664–667, 632, 672–673, 736; 356/39–41; 436/68; 604/264, 280

[56] References Cited

U.S. PATENT DOCUMENTS

| | | |
|---|---|---|
| 3,866,599 | 2/1975 | Johnson . |
| 4,340,615 | 7/1982 | Goodwin et al. ............. 128/635 X |
| 4,710,623 | 12/1987 | Lipson et al. . |
| 4,752,115 | 6/1988 | Murray et al. . |
| 4,798,207 | 1/1989 | Wade ........................... 128/637 X |
| 4,830,013 | 5/1989 | Maxwell . |
| 4,854,321 | 8/1989 | Boiarski . |
| 4,889,407 | 12/1989 | Markle et al. ............... 128/634 X |
| 4,900,933 | 2/1990 | Nestor et al. . |
| 4,951,669 | 8/1990 | Maxwell et al. . |
| 4,989,606 | 2/1991 | Gehrich et al. . |
| 5,005,576 | 4/1991 | Gunther ........................ 128/634 |
| 5,120,510 | 6/1992 | Gourley et al. ............. 128/634 X |

FOREIGN PATENT DOCUMENTS

| | | |
|---|---|---|
| 0015075A1 | 9/1980 | European Pat. Off. . |
| 0083969A3 | 7/1983 | European Pat. Off. . |
| 0253559A1 | 1/1988 | European Pat. Off. . |
| 0336984A1 | 10/1989 | European Pat. Off. . |
| 3038831 | 7/1982 | Fed. Rep. of Germany . |
| WO90/01894 | 3/1990 | PCT Int'l Appl. . |
| 1116766 | 6/1968 | United Kingdom . |

OTHER PUBLICATIONS

*Optex Diomedical, Inc.*, (12 pages).
European Search Report dated Jan. 25, 1994 for European Application No. EP 93 10 8179.
"Fiberoptic pH Probe Design" (FIG. 8).

Primary Examiner—Angela D. Sykes
Attorney, Agent, or Firm—Gary L. Griswold; Walter N. Kirn; Dale E. Hulse

[57] ABSTRACT

An assembly for insertion into the cardiovascular system of a patient comprising a catheter having first and second lumens and a distal port. The first lumen opens at the distal port. A probe is received in the second lumen. The probe includes a sensor responsive to a constituent of blood for providing a signal which is related to the constituent. The catheter has a window for allowing the constituent of blood to pass from outside the catheter to the sensor while substantially preventing other constituents of blood from passing from the outside of the catheter to the sensor.

31 Claims, 5 Drawing Sheets

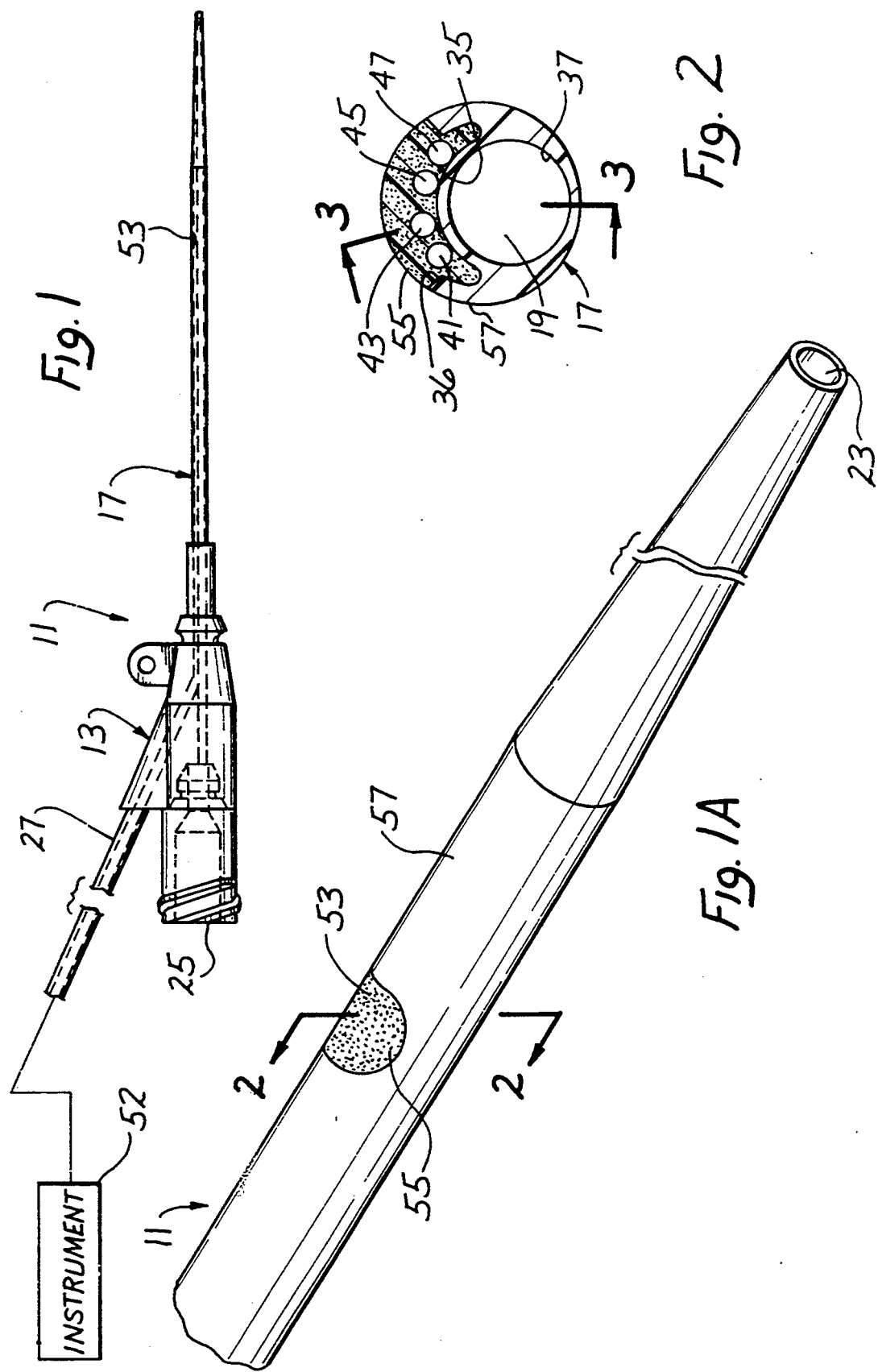

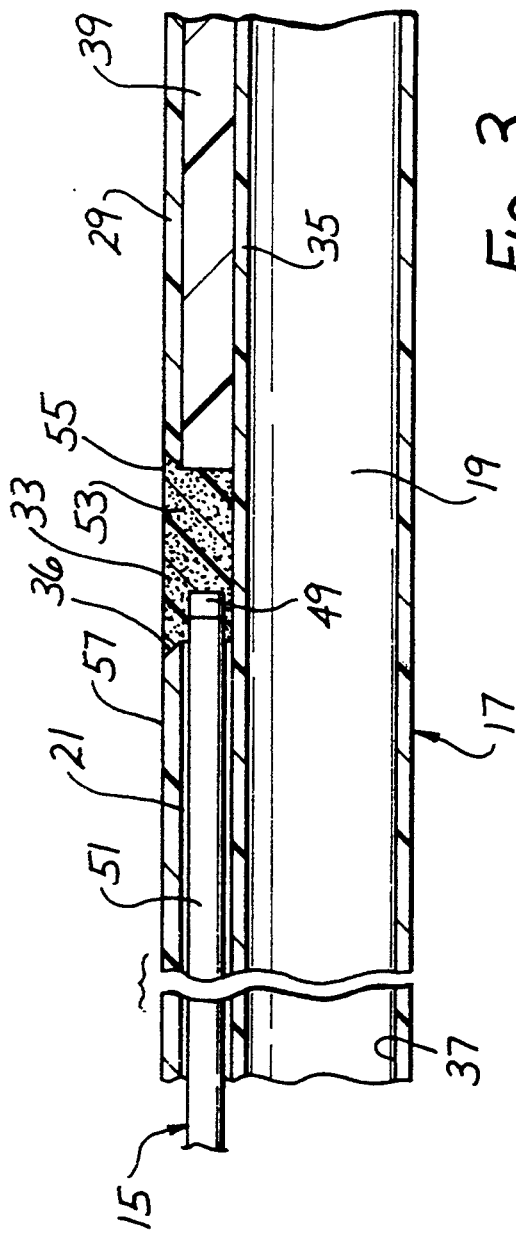
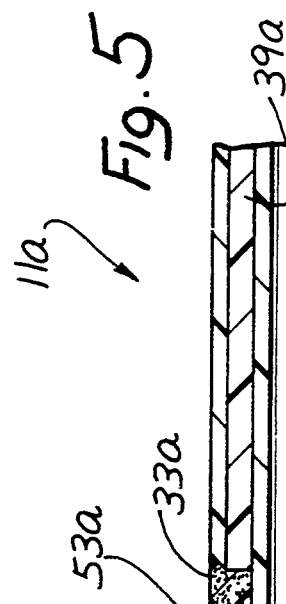
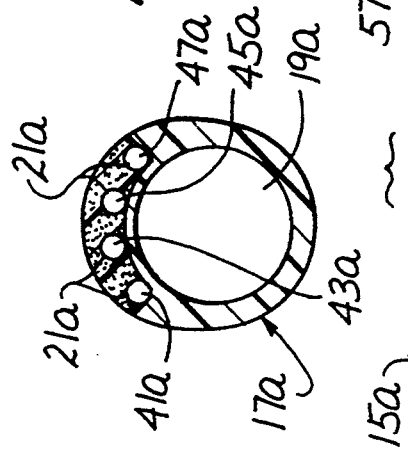

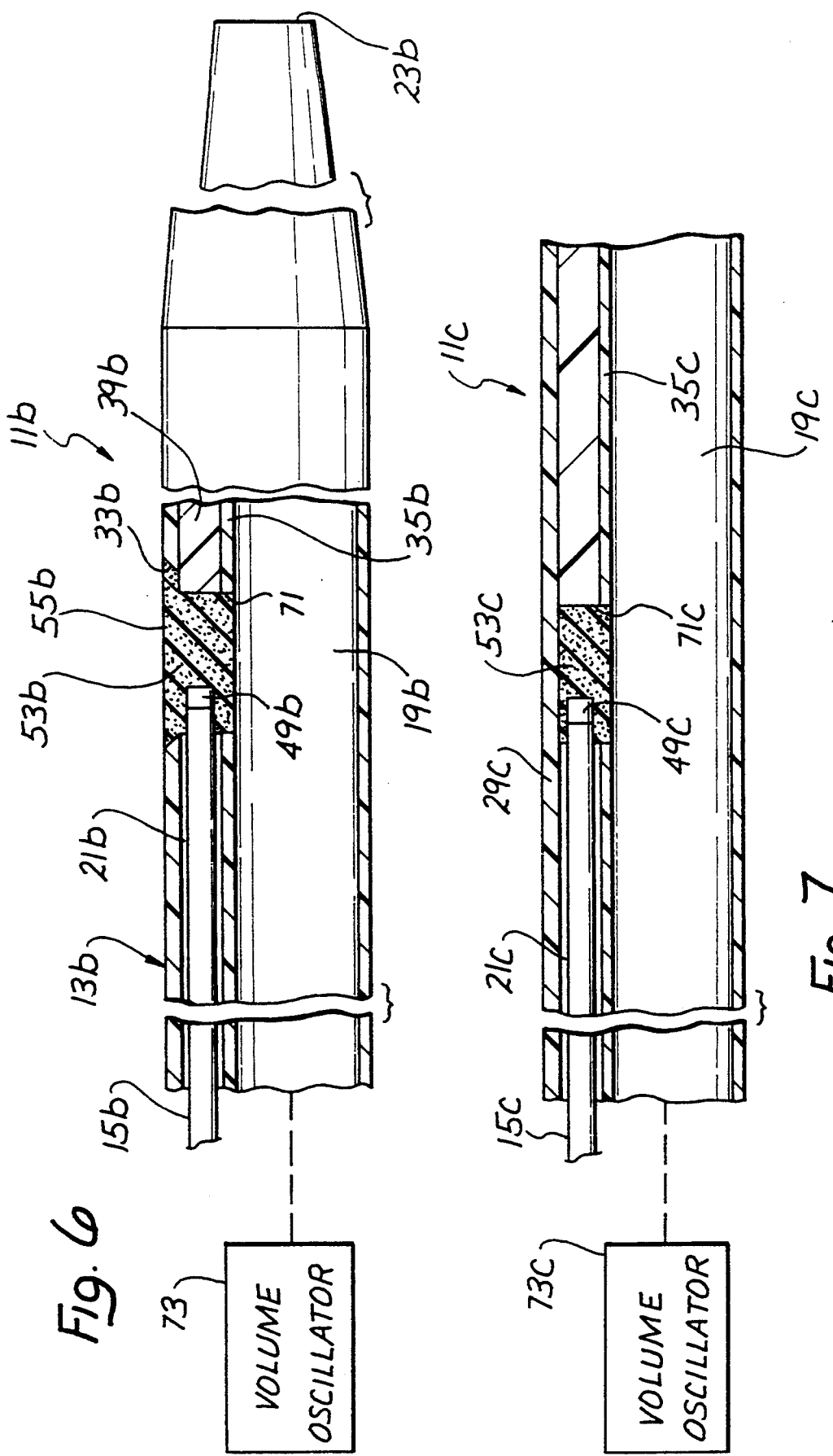

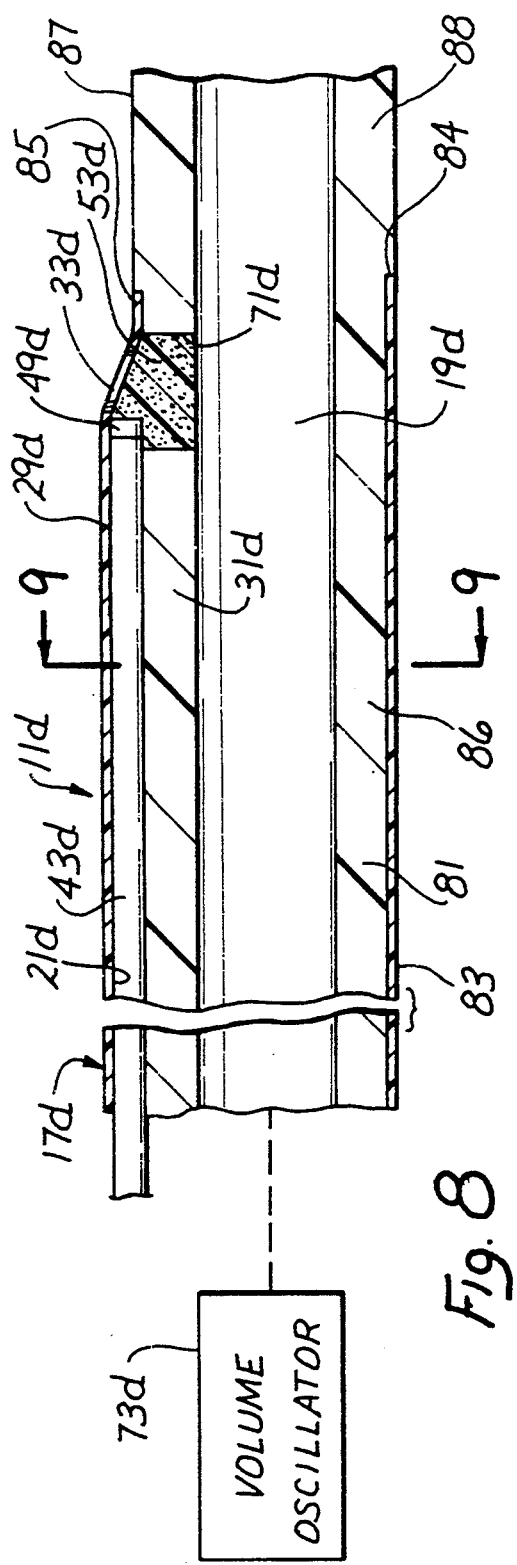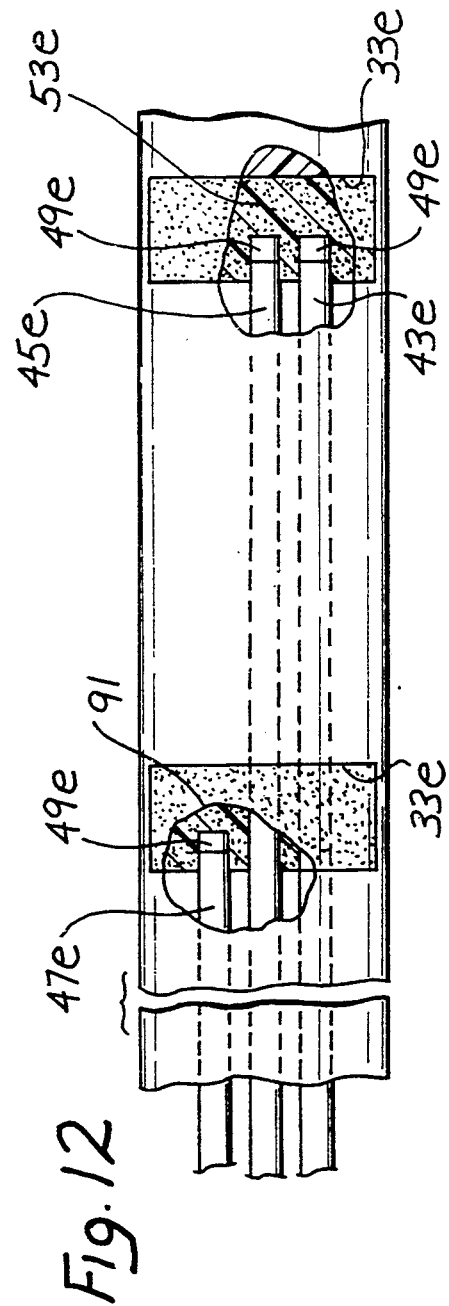

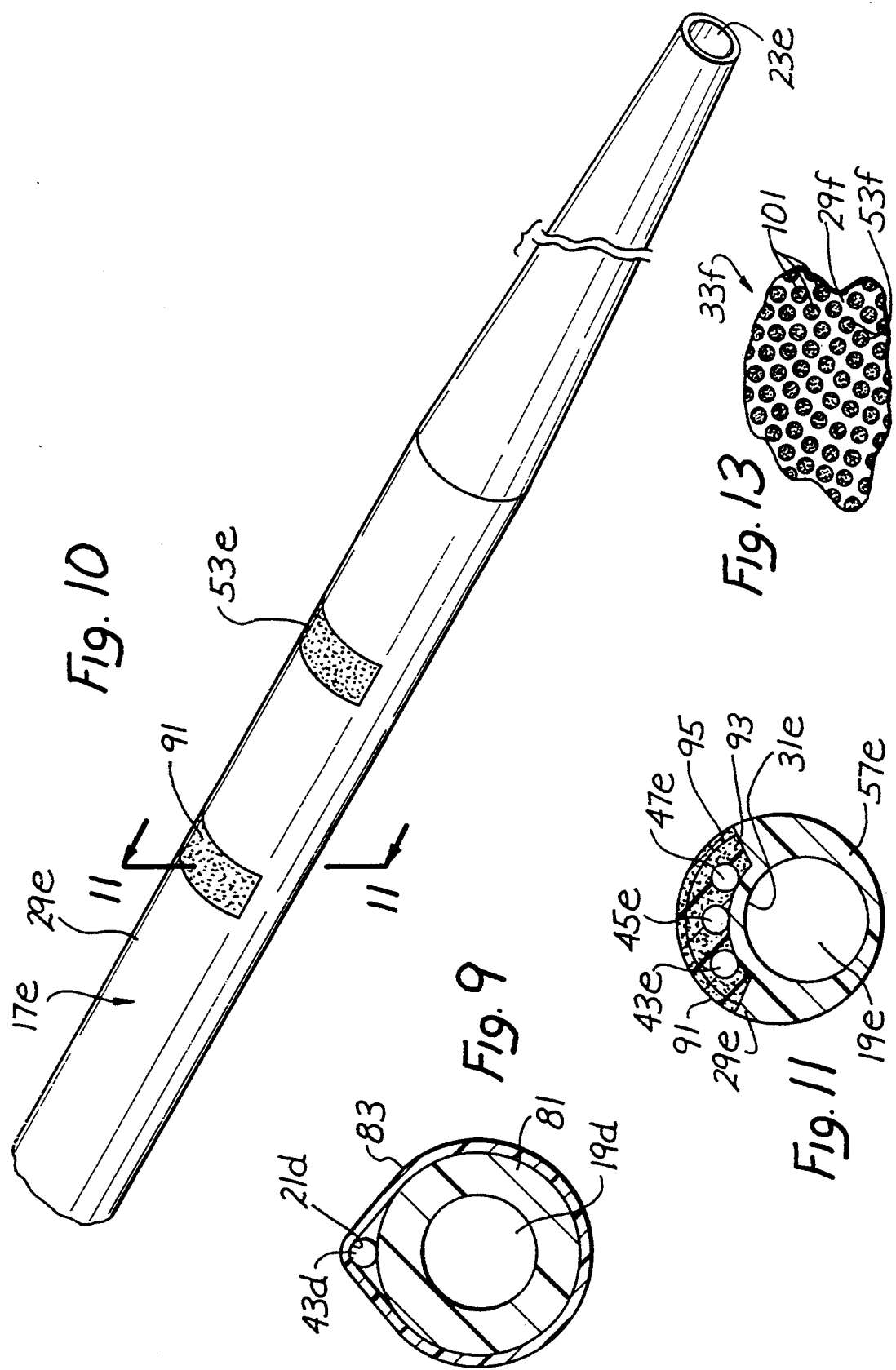

CATHETER AND PROBE-CATHETER ASSEMBLY

BACKGROUND OF THE INVENTION

It is sometimes necessary or desirable to measure the presence and/or concentration of blood constituents, such as blood gases, hydrogen ions other electrolytes, glucose, red blood cells and the like. This can be accomplished continuously and in real time in a patient undergoing surgery or intensive care by utilizing a catheter and a probe. The probe includes one or more sensors which are responsive to the constituent or compositional parameter of interest to provide a signal related to such constituent. One such system is shown in Maxwell U.S. Pat. No. 4,830,013.

According to the Maxwell patent, the accuracy of the blood constituent measurement system can be improved by keeping the sensor from contacting the wall of the vessel into which the catheter and probe are inserted. In one form illustrated in the Maxwell patent, this is accomplished by positioning the sensor within the lumen of the catheter and adjacent the distal opening of the catheter.

In another blood gas measurement system shown in Nestor et al U.S. Pat. No. 4,900,933, a dual-lumen catheter is provided with one lumen being used for fluid infusion and the other lumen being used for the probe. In the Nestor et al construction, the probe and the sensor of the probe are located outside the lumen distally of the distal end of the lumen. Accordingly, this sensor would appear to be subject to providing inaccurate readings as a result of contact with the wall of the vessel into which it is inserted and also appear to be subject to thrombus deposition of, for example, protein and platelets. In addition, the sensor would also appear to be relatively difficult to clean.

SUMMARY OF THE INVENTION

This invention provides a novel assembly for the measurement of constituent or compositional parameters of blood which provides many advantages and which overcomes the disadvantages noted above. This invention utilizes a multiple-lumen catheter with a first of the lumens being open to facilitate the performance of various tasks, including blood pressure measurement, blood sample withdrawal, infusion, etc. A second lumen of the catheter receives the probe. However, unlike the Nestor et al construction, the sensor is within the catheter and outside the first lumen. Because the sensor is inside the catheter, the catheter can be used to shield the sensor from some of the effects which tend to reduce the accuracy of the constituent measurement.

An important feature of this invention is that the catheter allows the constituent of blood to pass from outside the catheter to the sensor while substantially preventing unwanted constituents of blood, e.g., cellular constituents, from passing from outside the catheter to the sensor. In other words, the sensor can sense and respond to the constituent of blood without being immersed in the blood.

The risk of clotting increases as the exposed surface area of a foreign object within that body increases. An important advantage of this invention is that the exposed surface area of the probe and catheter is no greater than the exposed surface area of the catheter alone. Consequently, the probe and catheter create no more risk of clotting than the catheter alone. In addition, because the probe is substantially prevented from contacting the blood, the sensor is not subject to thrombus formations which would reduce the accuracy of the constituent measurement.

Various different paths can be used for passage of the constituent from outside the catheter to the sensor. One preferred path extends from outside the catheter to the sensor without passing through the first lumen. Such a path may be through an exterior wall of the catheter. Alternatively, the catheter may have a dividing wall between the first and second lumens, and the path may extend from the first lumen through the dividing wall to the sensor. Alternatively, both of the above-described paths may be employed.

A preferred way for defining the path is to employ a window in communication with the sensor and the exterior of the catheter. The window is selectively permeable to the constituent of blood which is of interest and substantially impermeable to various blood constituents which are not desired at the sensor.

One important advantage of using a window is that it can be relatively easily cleaned, and this is particularly true if the window is located on either the periphery of the first lumen or on the periphery of the catheter. In the former case, the window can be easily cleaned by a fast flush through the first lumen, and in the second case, the window is cleaned by blood in the vessel rushing past the window. In both cases, there is relatively high shear resulting from the fluid flowing past the window to provide the desired cleaning effect.

The location of the window will depend upon the desired path for the constituent of blood. For example, in one form of the invention, the catheter has an exterior wall with an opening leading to the second lumen, and the window is located to allow the constituent to pass from the exterior of the catheter into the opening and through the window to the sensor. Alternatively, the entire catheter can form the window.

If desired, the opening may be at the distal end of the second lumen. However, in a preferred construction, the exterior wall includes a peripheral wall, and the opening is in the peripheral wall. If desired, the window can form a concavity or protrude radially outwardly of the peripheral wall and form, in effect, a convex bump or protrusion on the periphery of the catheter. In this event, the sensor may be located within the protrusion or at any suitable location radially inwardly of the protrusion. However, this construction is more likely to be subject to thrombus deposition. Accordingly, it is preferred to substantially fill the opening in the peripheral wall with the window and provide a smooth surface on the window which blends with the outer surface of the peripheral wall so that the catheter presents a smooth, exterior surface to the passage of blood over it. This reduces the likelihood of thrombus deposition on the window, facilitates cleaning of the window by the flow of blood past the window and reduces the likelihood of contact between the vessel wall and the window.

The catheter has a dividing wall between the first and second lumens with an opening leading from the first lumen to the second lumen. The window may be located to allow the blood constituent to pass from the first lumen into the opening and through the window to the sensor. The window may protrude radially inwardly from the opening in the dividing wall and project into the first lumen. However, this is not preferred because of the discontinuity in the blood flow path that such a projection would provide. Preferably the surface of the window fills the opening and blends smoothly with the periphery of the first lumen to provide a minimal discontinuity to flow through the first lumen. This window feature may be provided as an alternative, or in addition to, the placement of the window in communication with the opening in the exterior wall.

In a broad sense, the sensor may be located anywhere between a location radially outwardly of the peripheral wall of the catheter body and a location just within the first or through lumen so long as the window is appropriately located to substantially prevent blood from passing to the sensor. However, to avoid the problems noted above, as well as preventing partial obstruction of the first lumen with the window and sensor, it is greatly preferred to locate the sensor between the outer surface of the peripheral wall of the catheter body and the periphery of the first lumen. Although the sensor may be located wholly or partially within the opening in the exterior wall or the opening in the dividing wall, the preferred location for the sensor is in the second lumen.

To provide the sensor with a rapid response, it is desirable to position the sensor closely adjacent the window, and preferably the sensor is in substantial engagement with the window. To assure that this relative positioning of the sensor and window is maintained, the sensor can be embedded in the window. Alternatively or in addition thereto, the second lumen may be sufficiently small so as to confine and position the probe and sensor.

This invention may be practiced with one or more probes and a corresponding number of sensors. When multiple probe sensors are used, they may be provided in the second lumen, or separate lumens may be used for each of the probes. If multiple sensors are used, they may be offset axially and/or circumferentially. In one construction, first and second sensors are axially offset, and separate windows are employed for each of the sensors. One advantage of this is that the two windows may be of different materials to pass different constituents of blood to each of the two sensors. For example, one of the windows may be selectively permeable to a blood gas and the other may be selectively permeable to hydrogen ions to enable the two sensors to respond to blood gas and pH, respectively.

The window should pass the constituent of interest which is commonly a blood gas or hydrogen ions and substantially excludes other constituents of blood. The window should also be capable of being strongly adhered to the catheter body, be biocompatible, have a relatively fast response time for the constituent which it passes, be durable to withstand use in a catheter and be capable of providing a smooth surface. Virtually any material meeting these criteria can be used for the window. For example, silicone, which is selectively permeable to oxygen and carbon dioxide, can be used for the window when the constituent is a blood gas, such as oxygen or carbon dioxide. A cellulose membrane is selectively permeable to hydrogen ions and blood gases and can be used for both.

By way of further example, the window may comprise multiple layers. For example, the window may include an inner layer of a porous polymer and an outer layer of a more dense polymer which is selectively permeable to the blood constituent of interest. In this event, the inner layer will provide a skeletal support for the outer layer and have very fast response due to its porous nature. The inner layer, which may be, for example, polyurethane or polysulfone, is not relied upon for selectivity. The outer layer, which may be a dense selective polymer, may be in the form of a thin skin over the inner layer. For example, the outer layer may be cellulose or any other dense, selectively permeable polymer.

In one preferred construction, the opening in the wall of the catheter includes a plurality of holes, and the window is at least partially in the plurality of holes. Each hole of a group of the holes may have a small diameter, and the window is located at least partially in such group of holes. One advantage of this construction is that the small-diameter holes strongly retain the material of the windows to even further reduce the likelihood that any of the window material might separate from the remainder of the catheter. In addition, by using a plurality of holes having a total area equal to the area of a single larger hole, the strength of the catheter body in the region of the holes in bending is not reduced as much as if such single larger hole were employed. Consequently, the likelihood of the catheter body kinking as a result of being subjected to bending forces is correspondingly reduced. Also, by using a plurality of holes having a total area equal to the area of a single larger hole, the time response of the multi-hole embodiment is about the same as the single hole.

The catheter may be of various different constructions and may include a conventional dual-lumen catheter body. Alternatively, the catheter body may include a first tube having the first lumen therein and a second tube over the first tube to define with the first tube the second lumen. Preferably, but not necessarily, the second tube includes shrink tubing. The first tube has a peripheral surface, the second lumen has a distal end, and the shrink tubing has a distal end portion. The shrink tubing, which is shrunk over the peripheral surface of the first tube, closes the distal end of the second lumen. This construction may be used, for example, to shrink the shrink tubing over the probe and the tube.

This invention may be embodied in an assembly which includes both a catheter and a probe or in a catheter which is adapted to receive a probe. Thus, many features of the invention are applicable to the catheter per se and to the catheter-probe combination. In the catheter-probe combination, the probe may be a separate member inserted into the second lumen of the catheter or the catheter may be formed over the probe to thereby create a second lumen in which the probe is located. In this latter case, the catheter may be, for example, molded or extruded over the probe.

Although the invention has been described above with reference to a sensor which is responsive to a blood constituent, in a broader sense, the invention is also applicable to an assembly which includes a sensor responsive to a constituent of a body fluid. In this event, the assembly is inserted into a region of a patient which contains the body fluid, and the window is selectively permeable to the constituent of interest and substantially prevents other components of the body fluid from passing through the window to the sensor. For example, the assembly may be used to measure or detect a constituent of cerebral spinal fluid.

The invention, together with additional features and advantages thereof, may best be understood by reference to the following description taken in connection with the accompanying illustrative drawings.

BRIEF DESCRIPTION OF THE DRAWINGS

FIG. 1 is a side elevational view of one form of assembly constructed in accordance with the teachings of this invention.

FIG. 1A is an enlarged, fragmentary, perspective view of a distal end portion of the assembly with the window enlarged for clarity.

FIG. 2 is an enlarged sectional view taken generally along line 2—2 of FIG. 1A.

FIG. 3 is a fragmentary sectional view taken generally along line 3—3 of FIG. 2.

FIGS. 4 and 5 are sectional views similar to FIGS. 2 and 3, respectively, illustrating a second embodiment of the invention.

FIGS. 6 and 7 are fragmentary sectional views similar to FIG. 3 illustrating third and fourth embodiments, respectively, of the invention.

FIG. 8 is a fragmentary sectional view similar to FIG. 3 illustrating a fifth embodiment of the invention.

FIG. 9 is a sectional view taken generally along line 9—9 of FIG. 8.

FIG. 10 is a fragmentary perspective view similar to FIG. 1A illustrating a sixth embodiment of the invention.

FIG. 11 is an enlarged, sectional view taken generally along line 11—11 of FIG. 10.

FIG. 12 is a fragmentary plan view of the construction shown in FIGS. 10 and 11 with portions broken away.

FIG. 13 is a fragmentary, top plan view illustrating another preferred way of providing an opening in a window.

DESCRIPTION OF THE PREFERRED EMBODIMENT

FIG. 1 shows an assembly 11 which generally comprises an elongated catheter 13, such as a radial artery or femoral artery catheter, and a probe assembly 15 (FIG. 3). Although the catheter 13 may be of various different constructions, in this embodiment, it includes a catheter body 17, a first or through lumen 19 (FIGS. 2 and 3), a second or probe lumen 21, a distal port 23 at which the through lumen opens, a fitting 25 and a conduit 27 coupled to the catheter body 17 in communication with the lumens 19 and 21, respectively. In this embodiment, the through lumen 19 is open and unobstructed by any component of the assembly 11, and although the distal port 23 can be located in various different positions along the length of the catheter body 17, in this embodiment, it opens axially at the distal end of the catheter body.

The catheter body 17 has an exterior wall, which in this embodiment, includes a peripheral wall 29 with an opening 33 leading to the probe lumen 21 and a dividing wall 35 between the lumens 19 and 21. Although the opening 33 can be of various different configurations, in this embodiment, it is round and has a beveled edge 36. In this embodiment, the dividing wall 35 is imperforate, and as shown in FIGS. 2 and 3, the through lumen 19 has a smooth, circular periphery 37.

The probe lumen 21 is of smaller cross-sectional area than the through lumen 19. The distal end of the probe lumen is closed in any suitable manner, such as by a plug 39.

The catheter body 17 is elongated and flexible. The catheter body 17 is constructed of a suitable, biocompatible polymeric material.

The probe assembly 15 comprises one or more probes and, in this embodiment, comprises probes 41, 43, 45 and 47 (FIG. 2). Each of the probes 41, 43, 45 and 47 includes a sensor 49 (only one being shown in FIG. 3) at the distal tip of the probe. Each of the sensors 49 is responsive to a parameter of blood for providing a signal which is related to the associated parameter of blood and transmission means 51 for transmitting a signal from the associated sensor. Although many different constructions and arrangements can be employed, in this embodiment, the probe 41 is a temperature probe, the sensor 49 of the probe 41 is a thermocouple, and the transmission means 51 of the probe 41 comprises electrical conductors. The present invention is not particularly concerned with the temperature probe 41.

The sensors 49 of the probes 43, 45 and 47 are responsive to a constituent of blood; specifically, oxygen, carbon dioxide and pH, respectively, and provide signals which are related to the associated constituent of blood. Although the sensors may be of virtually any kind, including electrical or optical, preferably, the sensors 49 for the probes 43, 45 and 47 are each fluorescent sensors, and each of the transmission means 51 for these three probes is, or includes, an optical fiber. The sensing of constituents of blood in vivo utilizing a catheter, a probe and fluorescent sensors is discussed in Maxwell U.S. Pat. No. 4,830,013 which is incorporated by reference herein. In any event, by directing exciting light along the transmission means 51 for the probes 43, 45 and 47, the associated sensors 49 respond to the partial pressures of oxygen and carbon dioxide and to the hydrogen ions, respectively, and provide fluorescent signals back along the associated transmission means 51 to the proximal end of the catheter 13 where a known instrument 52 (FIG. 1) converts the signals to discernable measurements of these constituents of blood.

The catheter 13 includes means for allowing the constituent of blood to pass from outside the catheter to the sensors 49 while substantially preventing unwanted components or constituents of blood from passing from outside the catheter to the sensors. In this embodiment, this is accomplished by a semi-permeable window 53 which is in communication with the sensors 49 and the exterior of the catheter 13. The window 53 is selectively permeable to relatively small molecules of the constituents of blood of interest. Thus, in this example, the window 53 is permeable to oxygen, carbon dioxide and hydrogen ions from blood, but substantially excludes other blood constituents. The window 53 may be constructed of, for example, cellulose or other suitable biocompatible material possessing this property. Alternatively, the window 53 may comprise a blood gas permeable portion in communication with the exterior of the catheter 13 and the sensors 49 of the oxygen and carbon dioxide probes 43 and 45 and a hydrogen ion permeable portion in communication with the exterior of the catheter and with the sensor 49 of the pH probe 47. By way of example, in this latter case, the blood gas permeable portion of the window 53 may comprise silicone, and the pH portion of the window 53 may comprise cellulose or phase-inverted polyurethane.

Regardless of the materials employed for the window 53, a path is provided for the constituents of interest which extends from outside the catheter 13 without passing through the through lumen 19. More specifically, the path extends through the opening 33 of the peripheral wall 29 and the window 53 to the sensors 49.

In this embodiment, the probe assembly 15 is received in the probe lumen 21, and all of the sensors 49 are within the probe lumen. In addition, in this embodiment, the sensors 49 are in substantial engagement with the window 53 and, in fact, are embedded in the window 53 so as to assure intimate contact between all of the exterior surfaces of the sensors 49 and the window 53. The construction is such that the sensors 49 are all close to the surface 55 so that the distance through which the blood parameters must pass to contact the sensors is minimized to improve the response time. The window 53 completely fills the opening 33 and the probe lumen 21 radially inwardly of the opening. The window 53 provides a smooth surface 55 which smoothly blends with a smooth outer surface 57 of the peripheral wall 29 as shown in FIGS. 1A, 2 and 3 so that the surface 55 does not form a projection or depression in the surface 57. Preferably, the periphery 37 and the surfaces 55 and 57 are heparin coated.

Preferably, the probe assembly 15 is received in the probe lumen 21 and suitably fixedly attached to the catheter 13 so as to form a unitary assembly. However, if desired, the catheter 13 and the probe assembly 15 may be separate elements which are assembled prior to or during use. In this event, the conduit 27 preferably forms an axial extension of the probe lumen 21 to facilitate insertion of the probe into the catheter.

In use, the assembly 11 is inserted into the body region of interest, such as the radial artery, using known techniques such that the window 53 is in contact with blood flowing through the radial artery. The window 53 is permeable to oxygen, carbon dioxide and pH ions of the blood so that the sensors 49, when subjected to an excitation light signal via the associated transmission means 51, can provide fluorescent signals along the associated transmission means 51 to the instrument 52 where these signals are converted into measurements of the constituents of interest which, in this embodiment, are the partial pressure of oxygen, the partial pressure of carbon dioxide and pH level. Because of the smooth surface 55 and its smooth blending to the smooth outer surface 57 the tendency of thrombus formations to occur at the window 53 is minimized. Moreover, the relatively fast flow and correspondingly high shear rate of blood over the surfaces 55 and 57 tend to provide a continuous cleaning action for the window 53. Because the probe assembly 15 is shielded from contacting the blood, the exposed surface area of the catheter 13 and the probe assembly 15 within the patient is no greater than the exposed surface area of the catheter 13 alone. The temperature probe 41 can sense the temperature of the blood through the window 53 or the peripheral wall 29 of the catheter body 17 and provide a temperature signal to the instrument 52. An appropriate anti-clotting solution, such as a heparinized saline solution can be introduced through the through lumen 19 to reduce the likelihood of clotting.

FIGS. 4 and 5 show an assembly 11a which is identical to the assembly 11 in all respects not shown or described herein. Portions of the assembly 11a corresponding to portions of the assembly 11 are designated by corresponding reference numerals followed by the letter "a." The primary difference between the assemblies 11 and 11a is that the assembly 11a has separate probe lumens 21a for each of the probes 41a, 43a, 45a and 47a as shown in FIG. 4. With this construction, each of the probe lumens 21a tends to confine and restrict the movement of the associated probe. Each of the probe lumens 21a has its distal end closed as with separate plugs 39a. In the construction of FIGS. 4 and 5, the opening 33a provides a well or chamber into which all of the probe lumens 21a open, and the sensors 49a of each of the probes are received in this well. The window 53a completely fills the well around the sensors 49a and has a smooth outer surface 55a which blends with the smooth outer surface 57a as described above in connection with the assembly 11.

Finally, the assembly 11a differs from the assembly 11 in the configuration of the cross section of the catheter body 17a. This difference in cross-sectional configuration, which is purely illustrative, can be seen by comparing FIGS. 2 and 4. The assembly 11a can be used and operated in the manner described above for the assembly 11.

FIGS. 6 and 7 show assemblies 11b and 11c, respectively, both of which are identical to the assembly 11 in all respects not shown or described herein. Portions of the assemblies 11b and 11c corresponding to portions of the assembly 11 are designated by corresponding reference numerals followed by the letters "b" and "c" respectively The primary difference between the assemblies 11b and 11 is that the window 53b also provides a path for the constituent of blood which extends from outside the catheter 13b through the distal port 23b, the through lumen 19b, an opening 71 in the dividing wall 35b and the window 53b to the sensor 49b. This path is in addition to the path from outside the catheter through the opening 33b and the window 53b to the sensor 49b.

One advantage of this inside sensing feature, i.e., receiving the blood parameters through the through lumen 19b, is that contact between the outer surface 55b and the wall of the vessel in which the catheter 13b is inserted will not interrupt the flow of the blood parameters to the sensors 49b. Also, by occasionally drawing blood into the lumen 19b, it can be determined if the window 53b is contacting the vessel wall.

When inside sensing is to be used, it is important to have the window 53b located so that it will contact sufficient blood in the through lumen 19b to achieve accurate constituent measurements. This can be accomplished, for example, by locating the window 53b and the opening 71 closely adjacent the distal port 23b and allowing the pressure of the blood created by the patient's heartbeats to force blood into the through lumen 19b sufficiently to permit accurate measurements to be made of the constituents of blood. Alternatively, a form of volume oscillator 73 may be employed to draw blood from the artery of the patient through the distal port 23b and into the through lumen 19b. The volume oscillator 73 may be of any type known in the art, such as a piston-cylinder device of the type shown in Maxwell U.S. Pat. No. 4,830,013 and Maxwell et al U.S. Pat. No. 4,951,669 or a syringe as shown by way of example in Gehrich et al U.S. Pat. No. 4,989,606.

The primary difference between the assembly 11c and the assembly 11 is that the assembly 11c has only inside sensing capabilities. Thus, in the assembly 11c, the opening 33 of the assembly 11 is eliminated, and the dividing wall 35c has an opening 71c. Thus, the assembly 11c is identical to the assembly 11b, except that it is capable of inside sensing only, i.e., receiving the blood parameters of interest from the through lumen 19c through the window 53c and the sensors 49c.

FIGS. 8 and 9 show an assembly 11d which is identical to the assembly 11 in all respects not shown or described herein. Portions of the assembly 11d corresponding to portions of the assembly 11 are designated by corresponding reference numerals followed by the letter "d."

The assembly 11d differs from the assembly 11 in the construction of the catheter body 17d and in that it is capable of both inside and outside sensing. More specifically, the catheter body 17d includes an elongated, flexible tube 81 of a suitable biocompatible polymeric material and shrink tubing 83 shrunk over the tube to define with the tube the probe lumen 21d. The tubing 83 may be, for example, heat shrink or chemical shrink tubing. In this embodiment, there is only one probe lumen 21d and only one probe, i.e., the oxygen probe 43d, but this is purely illustrative as any desired numbers of the probe lumens and probes may be provided.

The shrink tubing 83 may also be shrunk over the probe 43d to securely capture and hold the probe in a fixed orientation relative to the tube 81. In this embodiment, the tube 81 has a shoulder 84 which separates a small diameter portion 86 from a large diameter portion 88.

The shrink tubing 83 has a distal end portion 85 which is shrunk onto the small diameter portion 86 at the shoulder 84 to close the distal end of the probe lumen 21d. The distal end portion blends smoothly with an outer peripheral surface 87 of the large-diameter portion 88. The opening 33d in the peripheral wall 29d formed by the shrink tubing 83 and the window 53d provide an outside sensing capability.

Inside sensing is provided by the opening 71d in the tube 81. In this embodiment, the wall of the tube 81 forms the dividing wall 31d between the through lumen 19d and the probe lumen 21d. Of course, the assembly 11d may be adapted solely for inside sensing by eliminating the opening 33d or solely for outside sensing by eliminating the opening 71d in the tube 81. To aid the inside sensing capability, the assembly 11d may include a volume oscillator 73d.

FIGS. 10–12 show an assembly 11e which is identical to the assembly 11 in all respects not shown or described herein. Portions of the assembly 11e corresponding to portions of the assembly 11 are designated by corresponding reference numerals followed by the letter "e."

The assembly 11e is characterized by having a distal window 53e and a proximal window 91. The oxygen probe 43e and the carbon dioxide probe 45e extend into the distal window 53e, and the pH probe 47e terminates in the proximal window 91. Although the assembly 11e may also incorporate a temperature probe, none is illustrated.

The distal window 53e in this embodiment is constructed of any selectively permeable media, such as silicone, which will pass oxygen and carbon dioxide and substantially exclude other unwanted blood constituents. Similarly, the window 91 may be constructed of any suitable material which will exclude blood and pass hydrogen ions to the sensor 49e of the pH probe 47e. In this embodiment, the window 91 comprises an inner layer 93 of a porous polymer, such as polyurethane or polysulfone, and an outer layer 95 of a dense, selectively permeable material, such as cellulose. Cellulose is selectively permeable to hydrogen oxygen ions so that the sensor 49e of the pH probe 47e can sense and respond to the pH level. This and similar multi-layer windows may be utilized in any of the embodiments of this invention. The window 91 has a smooth outer surface 97 which blends smoothly with the outer surface 57e in the manner described above for the surfaces 55 and 57 of the assembly 11.

The spacing between the windows 53e and 91 is not critical, but preferably they are relatively close together and relatively near the distal port 23e. As illustrated, the assembly 11e is adapted only for outside sensing, but it can be made to accommodate inside sensing as shown, for example, in FIG. 7 or for both outside and inside sensing as shown, for example, in FIG. 6.

To accommodate the windows 53e and 91, the catheter body 17e has proximal and distal openings 33e in the peripheral wall 29e. The openings 33e differ from the openings 33 of the assembly 11 in that they are generally rectangular as viewed in plan. Of course, this is merely illustrative in that the shape of these openings in all of the embodiments of this invention may be rounded, rectangular or of any other desired configuration.

FIG. 13 shows another preferred way to form an opening 33f which can be applied to any of the outside sensing embodiments of this invention. The technique shown in FIG. 13 can also be applied to any of the inside sensing embodiments of this invention.

In FIG. 13, the opening 33f comprises a plurality of grouped, closely spaced holes 101 of small cross-sectional area. For example, each of the holes 101 may be from about 10 to about 100 microns in diameter, and the center-to-center spacing of the holes may be, for example, about 2 hole diameters, although this is not at all critical. The total area of the holes 101 may be equal to the area of the opening 33 (FIG. 3).

The holes 101 are filled with the window 53f, and preferably, each of the holes 101 is completely filled with the material of the window. Consequently, the peripheral wall 29f series, in effect, as a matrix for containing the spaced apart segments of the window 53f. The holes 101 in the peripheral wall 29f can be formed, for example, by various known micro-machining techniques, including laser and chemical ablation. For inside sensing capability, the holes 101 can be formed, for example, in the dividing wall, such as the dividing wall 35b (FIG. 6), in any suitable manner, including micromachining techniques. If no outside sensing is needed or desired, any opening formed in the peripheral wall, such as the peripheral wall 29c (FIG. 7) as a result of formation of the holes 101 in the dividing wall 35c can be appropriately closed.

Although exemplary embodiments of the invention have been shown and described, many changes, modifications and substitutions may be made by one having ordinary skill in the art without necessarily departing from the spirit and scope of this invention.

We claim:

1. An assembly for insertion into a blood vessel of a patient comprising:

an elongated extruded catheter having first and second lumens and a distal port, said first lumen opening at a proximal end and opening at the distal port so as to allow the flow of fluid through said catheter and so as to provide fluid communication between said first lumen and the blood vessel of the patient, said second lumen having a closed end to prevent the flow of blood into said second lumen; and a probe including an optical sensor responsive to a constituent of the blood for providing a signal which is related to the constituent of the blood and said transmission means comprising an optical fiber;

said probe, including said optical sensor and said optical fiber, being received in the second lumen such that said optical sensor is within the catheter but outside the first lumen and not in contact with the blood in the blood vessel of the patient; and said catheter including means for allowing the constituent of the blood to pass from the blood to the optical sensor in the second lumen while substantially preventing at least some other components of the blood from passing from the blood to the optical sensor.

2. An assembly as defined in claim 1 wherein the means for allowing provides a path for the constituent which extends from outside the catheter to the sensor without passing through the first lumen.

3. An assembly as defined in claim 2 wherein the catheter has an exterior wall and said path extends from outside the catheter through the exterior wall to the sensor.

4. An assembly as defined in claim 3 wherein the exterior wall is a peripheral wall.

5. An assembly as defined in claim 1 wherein said means for allowing includes the first lumen.

6. An assembly as defined in claim 5 wherein the catheter has a dividing wall between the first and second lumens and the means for allowing provides a path for the constituent which extends from the first lumen through the dividing wall to the sensor.

7. An assembly as defined in claim 6 wherein the catheter has an exterior wall and said path also extends from outside the catheter through the exterior wall to the sensor.

8. An assembly as defined in claim 1 wherein said means for allowing the constituent of the blood to pass from the blood outside the catheter to the optical sensor comprises a window formed in an exterior wall of said catheter, said window being between the sensor and the blood outside the catheter, said window being selectively permeable to the constituent of blood and allowing the constituent to pass from the blood outside the catheter through the window to the sensor.

9. An assembly as defined in claim 8 wherein at least a portion of the window is in the second lumen substantially in engagement with the sensor.

10. An assembly as defined in claim 8 wherein the window substantially prevents nongaseous and nonionic constituents of blood from flowing through the window to the sensor.

11. An assembly as defined in claim 8 wherein the exterior wall includes a peripheral wall, the window is in the peripheral wall and provides a smooth surface, the peripheral wall has an outer surface and said smooth surface blends with the outer surface of the peripheral wall.

12. An assembly as defined in claim 8 wherein the catheter has a dividing wall between the first and second lumens with an opening leading from the first lumen to the second lumen, and a second window is located in said opening to allow the constituent to pass from the first lumen into the opening and through the window to the sensor.

13. An assembly as defined in claim 8 wherein said sensor is a first sensor and said window is a first window and the probe includes a second sensor and a second window, said second sensor being in the catheter outside said first lumen and spaced axially from the first sensor, said second sensor is adapted to provide a signal which is related to a constituent of blood which is different from the constituent to which the first sensor responds, said second window is in communication with the second sensor and the exterior of the catheter, said second window is permeable to the constituent of blood to which the second sensor responds.

14. An assembly as defined in claim 13 wherein the first window is permeable to a blood gas and the first sensor is responsive to the blood gas to provide said signal of the first sensor and the second window is permeable to hydrogen ions and the second sensor is responsive to the hydrogen ions to provide said signal of the second sensor.

15. An assembly as defined in claim 8 wherein the catheter includes a first tube having the first lumen therein and a second tube over the first tube to define with said first tube the second lumen.

16. An assembly as defined in claim 15 wherein the first tube has a peripheral surface, the second tube includes shrink tubing and the shrink tubing has a distal end portion which is shrunk over the peripheral surface of the first tube to form said closed end of the second lumen.

17. An assembly as defined in claim 8 wherein said exterior wall of said catheter has a plurality of holes and the window is at least partially in said plurality of holes.

18. An assembly as defined in claim 8 wherein the window includes silicone.

19. An assembly as defined in claim 8 wherein the window includes cellulose.

20. An assembly as defined in claim 8 wherein the window includes an inner layer of a porous polymer and an outer layer of a more dense polymer which is selectively permeable to the constituent of blood.

21. An assembly as defined in claim 8 wherein the window is selectively to a blood gas.

22. An assembly as defined in claim 8 wherein the window is selectively permeable to hydrogen ions.

23. An assembly as defined in claim 1 wherein said allowing means comprises a window positioned adjacent to said second lumen, said window being selectively permeable to the constituent of blood and allowing the constituent to pass from the blood through the window to the sensor.

24. An assembly as defined in claim 1 wherein said optical sensor senses a blood gas.

25. An assembly as defined in claim 1 wherein said optical sensor senses oxygen.

26. An assembly as defined in claim 1 wherein said optical sensor senses carbon dioxide.

27. An assembly as defined in claim 1 wherein said optical sensor senses hydrogen ions.

28. An assembly for insertion into the cardiovascular system or a patient comprising:

an elongated catheter having first and second lumens and a distal port, said first lumen opening at the distal port, said catheter having an exterior wall with an opening leading to the second lumen; and a probe including a sensor responsive to a constituent of blood for providing a signal which is related to the constituent of blood and transmission means for transmitting the signal from the sensor;

said probe being received in the second lumen and said sensor being within the catheter outside the first lumen; and said catheter including a window in communication with the sensor and the exterior of the catheter, said window being selectively permeable to the constituent of blood and located to allow the constituent to pass from the exterior of the catheter into the opening and through the window to the sensor, said window including an inner layer of a porous polymer and an outer layer of a more dense polymer which is selectively permeable to the constituent of blood.

29. An assembly for insertion into a region of a patient containing a body fluid comprising:

an elongated catheter having first and second lumens and a distal port, said first lumen opening at the distal port; and a probe including a sensor responsive to a constituent of the body fluid for providing a signal which is related to the constituent of the body fluid and transmission means for transmitting the signal from the sensor;

said probe being received in the second lumen and said sensor being within the catheter outside the first lumen; and said catheter including means for allowing the constituent of the body fluid to pass from outside the catheter to the sensor while substantially preventing at least some other components of the body fluid from passing from outside the catheter to the sensor, said allowing means comprising an inner layer of a porous polymer and an outer layer of a more dense polymer which is selectively permeable to the constituent of the body fluid.

30. An assembly as defined in claim 29 wherein said sensor senses a blood gas.

31. An assembly as defined in claim 29 wherein said sensor senses hydrogen ions.

* * * * *

UNITED STATES PATENT AND TRADEMARK OFFICE
CERTIFICATE OF CORRECTION

PATENT NO. : 5,333,609
DATED : August 2, 1994
INVENTOR(S) : William Bedingham et al.

It is certified that error appears in the above-indentified patent and that said Letters Patent is hereby corrected as shown below:

Col. 1, line 7, after "ions" insert --(pH),--.

Col. 11, line 1, before "said" please insert --transmission means for transmitting the signal from the sensor,--.

Col. 12, line 7, after "catheter," insert --and--.

Col. 12, line 39, claim 21, line 2, after "selectively" insert --permeable--.

Col. 12, line 57, claim 28, line 2, "or" should be --of--.

Signed and Sealed this

Second Day of May, 1995

*Attest:*

BRUCE LEHMAN

*Attesting Officer*   *Commissioner of Patents and Trademarks*